US005605917A

United States Patent [19]
Ogletree

[11] Patent Number: 5,605,917
[45] Date of Patent: Feb. 25, 1997

[54] METHOD OF TREATING DYSMENORRHEA EMPLOYING AN INTERPHENYLENE 7-OXABICYCLOHEPTYL SUBSTITUTED HETEROCYCLIC AMIDE PROSTAGLANDIN ANALOG

[75] Inventor: Martin L. Ogletree, Newtown, Pa.

[73] Assignee: Bristol-Myers Squibb Company, Princeton, N.J.

[21] Appl. No.: 361,397

[22] Filed: Dec. 22, 1994

[51] Int. Cl.$^6$ .......... A61K 31/41; A61K 31/55; A61K 31/445; A61K 31/42

[52] U.S. Cl. .......... 514/365; 514/212; 514/325; 514/328; 514/374; 514/381; 514/899

[58] Field of Search .................. 514/318, 365, 514/374, 212, 324, 325, 381, 899

[56] References Cited

U.S. PATENT DOCUMENTS 5,100,889  3/1992  Misra et al. ............... 514/365

FOREIGN PATENT DOCUMENTS 2217597A  11/1989  United Kingdom ......... A61K 31/175

OTHER PUBLICATIONS

F. Bertolino, et al., "Intrinsic Activity of the Non–Prostanoid Thromboxane A2 Receptor Antagonist, Daltroban (BM 13,505), in Human Platelets invitro and in the Rat Vasculature invivo", Br. J. Pharm. 115:210–216 1995.

I. Miki, et al., "Differences in Activities of Thromboxane A2 Receptor Antagonists in Smoteh Muscle Cells", Eup. J. Pharm.–Mol. Pharm. Sect. 227:199–204 1992.

G. P. Dube, et al., "I Vivo Effects of a Novel Thromboxane A2/Prostaglandin H2 (TXA2/PGH2) Partial Agonist, (+)5(Z)–7[3–endo–phenylsulfonylamino[2.2.1] –bicyclohept–2–exo–yl]–heptenoic acid [(+)–S–145], Vascular, Platelet and Cardiac Function". 272(2):799–1995.

M. L. Ogletree, et al., "Pharmacological Profile of BMS180, 291:A Potent, Long–Acting, Orally Active Thromboxane A2/Prostaglandin Endoperoxide Receptor Antagonist", The J. Pharm and Espt. Ther. 264(2):570–578 1993.

*Primary Examiner*—John W. Rollins
*Attorney, Agent, or Firm*—Burton Rodney

[57]  ABSTRACT

A method is provided for treating dysmenorrhea (menstrual cramps) employing an interphenylene 7-oxabicycloheptyl substituted heterocyclic amide prostaglandin analog thromboxane $A_2$ receptor antagonist such as ifetroban, alone or in combination with a non-steroidal anti-inflammatory drug (NSAID).

15 Claims, No Drawings

METHOD OF TREATING DYSMENORRHEA EMPLOYING AN INTERPHENYLENE 7-OXABICYCLOHEPTYL SUBSTITUTED HETEROCYCLIC AMIDE PROSTAGLANDIN ANALOG

FIELD OF THE INVENTION

The present invention relates to a method for treating dysmenorrhea (menstrual cramps) employing an interphenylene 7-oxabicycloheptyl substituted heterocyclic amide prostaglandin analog thromboxane $A_2$ ($TXA_2$) receptor antagonist alone or in combination with a non-steroidal anti-inflammatory drug (NSAID).

BACKGROUND OF THE INVENTION

U.S. Pat. No. 5,100,889 to Misra et al discloses interphenylene 7-oxabicycloheptyl substituted heterocyclic amide prostaglandin analog $TXA_2$ antagonists having the structure

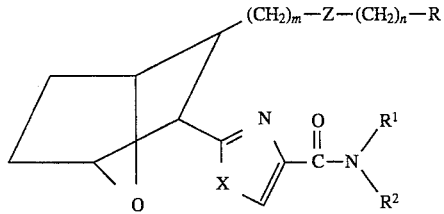

and including all stereoisomers thereof, wherein
m is 1, 2 or 3; n is 0, 1, 2, 3 or 4;
Z includes

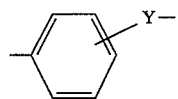

wherein Y is O, a single bond or vinyl (—CH=CH—), with the provisos that when n is 0, Y cannot be 0; and when Y=vinyl, n=0;
R is $CO_2H$, $CO_2$lower alkyl, $CO_2$alkali metal, $CH_2OH$, $CONHSO_2R^3$, $COHNR^{3a}$, or

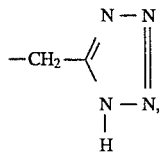

(—$CH_2$-5-tetrazolyl);
X is O, S or NH;
$R^1$ is hydrogen, lower alkyl, lower alkenyl, lower alkynyl, aralkyl, aryl, cycloalkyl, cycloalkylalkyl, cycloheteroalkyl, cycloheteroalkylalkyl, heteroaryl or heteroarylalkyl, or amide

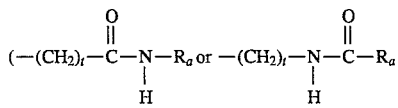

wherein t is 1 to 12 and $R_a$ is lower alkyl, aryl, cycloalkyl, or cycloalkylalkyl);

$R^2$ is hydrogen, lower alkyl, aryl, or aralkyl;
or
$R^1$ and $R^2$ together with the nitrogen to which they are linked may form a 5- to 8-membered ring;
$R^3$ is lower alkyl, aryl or aralkyl; and
$R^{3a}$ is hydrogen, lower alkyl, aryl or aralkyl.

The above Misra et al patent covers the thromboxane $A_2$ receptor antagonist BMS180,291 which has the structure

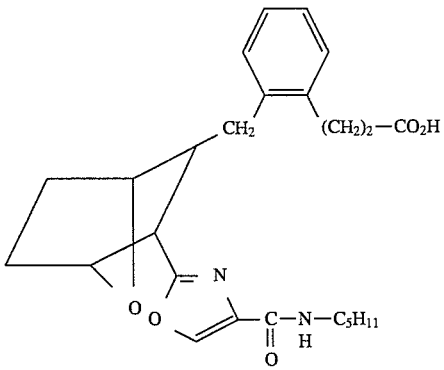

and the name [1S-(1α,2α,3α,4α)]-2-[[3-[4-[[pentylamino)carbonyl]-2-oxazolyl]-7-oxabicyclo[2.2.1]hept-2-yl]methyl]benzenepropanoic acid or a pharmaceutically acceptable salt thereof such as its sodium salt, potassium salt, calcium salt or magnesium salt.

For matter of convenience, BMS 180,291 will hereinafter be referred to as "ifetroban".

Published GB application 2217597A to National Research Development Corporation discloses use of compounds having thromboxane antagonist activity in the treatment of dysmenorrhea, endometriosis and fibroids, which may have the structure

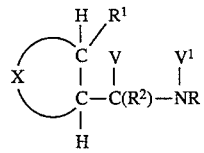

wherein

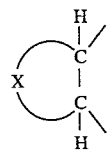

is a bicyclo-heptane, -heptene, -octane or -octene group, including

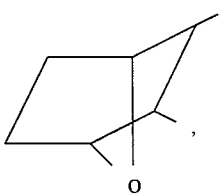

$R^1$ is a 6-carboxyhex-2-enyl group or modification thereof,
V and $V^1$ either each separately is H or together are the second bond of a C—N double bond;

$R^2$ is H, aliphatic hydrocarbon group or an aliphatic hydrocarbon group substituted by an aromatic group directly or through an O or S atom;

R is —NH.CO.NH—$R^3$ or —NH.CS.NH—$R^3$ where $R^3$ is an aliphatic hydrocarbon group, an aromatic group or an aliphatic hydrocarbon group substituted by one or more groups directly or through an O or S atom.

EP535924 and EP535923, each filed by Merck Frosst Canada, disclose various indole leukotriene inhibitors which have thromboxane antagonist activity, and thromboxane synthetase inhibitory activity, and which may optionally be used with an NSAID for treating dysmenorrhea.

U.S. Pat. No. 5,312,818 to Rubin et al discloses a combination of a thromboxane $A_2$ receptor antagonist and an anti-inflammatory agent to treat inflammatory conditions, such as arthritis, while inhibiting formation of and/or treating ulcers.

DESCRIPTION OF THE INVENTION

In accordance with the present invention, a method is provided for treating dysmenorrhea (menstrual cramps) wherein a therapeutic amount of an interphenylene 7-oxabicycloheptyl substituted heterocyclic amide prostaglandin analog $TXA_2$ receptor antagonist (such as ifetroban) alone or in combination with a non-steroidal anti-inflammatory drug, is systemically administered, such as orally or parenterally, to a mammalian species, to treat dysmenorrhea.

Where the method employs a combination of thromboxane antagonist and NSAID, the thromboxane $A_2$ receptor antagonist as defined above and a non-steroidal anti-inflammatory drug (NSAID) may be employed in a weight ratio to each other of within the range of from about 0.01:1 to about 100:1, and preferably from about 0.5:1 to about 2:1.

Non-steroidal anti-inflammatory drugs or agents which may be employed herein include, but are not limited to, aspirin, indomethacin, ibuprofen, meclofenamate, naproxen, diclofenac sodium, phenylbutazone and piroxicam.

Thromboxane $A_2$ receptor antagonists which may be employed herein are the interphenylene 7-oxabicycloheptyl substituted heterocyclic amide prostaglandin analogs of U.S. Pat. No. 5,100,889 to Misra et al (which is incorporated herein by reference) having the formula

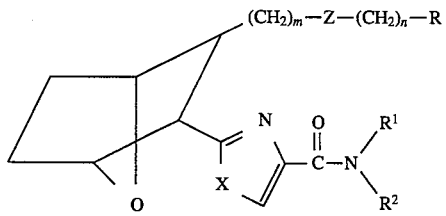

and including all stereoisomers thereof, wherein
m is 1, 2 or 3; n is 0, 1, 2, 3 or 4;
z includes

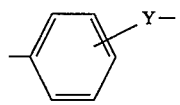

wherein Y is O, a single bond or vinyl (—CH=CH—), with the provisos that when n is 0, Y cannot be 0; and when Y=vinyl, n=0;

R is $CO_2H$, $CO_2$lower alkyl, $CO_2$alkali metal, $CH_2OH$, $CONHSO_2R^3$, $CONHR^{3a}$, or

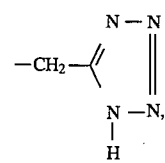

(—$CH_2$-5-tetrazolyl);

X is O, S or NH;

$R^1$ is hydrogen, lower alkyl, lower alkenyl, lower alkynyl, aralkyl, aryl, cycloalkyl, cycloalkylalkyl, cycloheteroalkyl, cycloheteroalkylalkyl, heteroaryl or heteroarylalkyl, or amide

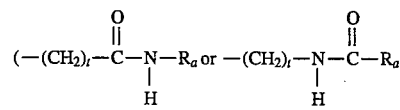

wherein t is 1 to 12 and $R_a$ is lower alkyl, aryl, cycloalkyl, or cycloalkylalkyl);

$R^2$ is hydrogen, lower alkyl, aryl, or aralkyl;
or $R^1$ and $R^2$ together with the nitrogen to which they are linked may form a 5- to 8-membered ring;

$R^3$ is lower alkyl, aryl or aralkyl; and $R^{3a}$ is hydrogen, lower alkyl, aryl or aralkyl.

Examples of thromboxane $A_2$ receptor antagonists suitable for use herein are the interphenylene 7-oxabicycloheptyl substituted heterocyclic amide prostaglandin analogs as disclosed in U.S. Pat. No. 5,100,889 which include

[1S-(1α,2α,3α,4α)]-2-[[3-[4[(4-cyclohexylbutyl) amino]carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[[4-chlorophenyl) butyl]amino]carbonyl]-2-oxazolyl]-7-oxabicyclo[2.2.1]hept-2-yl]methyl]benzenepropanoic acid or esters, or salts thereof;

[1S-(1α,2α,3α,4α)]-3-[[3-[3-[[(4-cyclohexylbutyl) amino]carbonyl]-2-oxazolyl]-7-oxabicyclo[2.2.1]hept-2-yl]methyl]benzeneacetic acid, or esters or salts thereof;

[1S-(1α,2α,3α,4α)]-[2-[3-[4-[[(4-cyclohexylbutyl)amino]carbonyl]-2-oxazolyl]-7-oxabicyclo[2,2,1]hept-2-yl]methyl]phenoxy]acetic acid, or esters or salts thereof;

[1S-(1α,2α,3α,4α)]-2-[[3-[4-[[(1-piperidinylbutyl)amino]carbonyl]-2-oxazolyl]-2-oxabicyclo[2.2.1]hept-2-yl]methyl]benzenepropanoic acid, or esters or salts thereof;

[1S-(1α,2α,3α,4α)]-2-[[3-[4-[[[4-(4-hydroxyphenyl)butyl]amino]carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[(propylamino)carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[(4-pentylamino)carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[(2-cyclohexylethyl)amino]carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[(5,5-dimethylhexyl)amino]carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[[4-(4-methoxyphenyl)butyl]amino]carbonyl]-2-oxazolyl]-7-oxabicyclo[2.2.1]hept-2-yl]methyl]benzenepropanoic acid, or esters or salts thereof;

[1S-(1α,2α,3α(E),4α)]-2-[3-[4-[[(4-cyclohexyl-2-butenyl) amino]carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[4-cyclohexylidenebutyl) amino]carbonyl]-2-oxazolyl]-7-oxabicyclo[2.2.1]hept-2-yl] methyl]benzenepropanoic acid, or esters or salts thereof;

[1S-(1α,2α,3α,4α)]-2-[[3-[4-[(heptylamino)carbonyl]-2-oxazolyl]-7-oxabicyclo[2.2.1]hept-2-yl]-methyl]benzenepropanoic acid, or esters or salts thereof;

[1S-(1α,2α,3α,4α)]-2-[2-[3-[4-[[(4-cyclohexylbutyl) amino]carbonyl]-2-oxazolyl]-7-oxabicyclo[2.2.1]hept-2-yl] ethyl]benzeneacetic acid, or esters or salts thereof;

[1S-(1α,2α,3α,4α)]-2-[2-[3-[4-[[(4-cyclohexylbutyl) amino]carbonyl]-2-oxazolyl]-7-oxabicyclo[2.2.1]hept-2-yl] ethyl]benzenepropanoic acid, or esters or salts thereof;

[1S-(1α,2α,3α,4α)]-2-[[3-[4-[decylamino) carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[[(4-cyclohexylbutyl) amino] carbonyl]-2-oxazolyl]-7-oxabicyclo [2.2.1]hept-2-yl]methyl]benzeneacetic acid, or esters or salts thereof;

[1S-(1α,2α,3α,4α)]-2-[[3-[4-[(cyclohexyl amino)carbonyl]-2-oxazolyl]-7-oxabicyclo[2.2.1 ]hept-2-yl]methyl]benzenepropanoic acid, or esters or salts thereof;

[1S-(1α,2α,3α,4α)]-2-[[3-[4-[[(1-methylethyl) amino] carbonyl]-2-oxazolyl]-7-oxabicyclo [2.2.1 ]hept-2-yl]methyl]benzenepropanoic acid or esters or salts thereof;

[1S-(1α,2α,3α,4α)]-2-[[3-[4-[[(8-cyclohexyloctyl) amino]carbonyl]-2-oxazolyl]-7-oxabicyclo[2.2.1]hept-2-yl] methyl]benzenepropanoic acid, or esters or salts thereof;

[1S-(1α,2α,3α,4α)]-3-[2-[3-[4-[[(4-cyclohexylbutyl) amino]carbonyl]-2-oxazolyl]-7-oxabicyclo[2.2.1]hept-2-yl] ethyl]benzoic acid, or esters or salts thereof;

[1S-(1α,2α,3α,4α)]-2-[[3-[4-[[[(4-(methylthiophenyl) butyl]amino]carbonyl]-2-oxazolyl]-7-oxabicyclo [2.2.1 ]hept-2-yl]methyl]benzenepropanoic acid, or esters or salts thereof;

[1S-(1α,2α,3α,4α)]-2-[[3-[4-[[[4-(4-methylsulfonylphenyl]butyl]amino]carbonyl]-2-oxazolyl]-7-oxabicyclo [2.2.1 ]hept-2-yl]methyl]benzenepropanoic acid, or esters or salts thereof;

[1S-(1α,2α,3α,4α)]-2-[[3-[4-[[(cyclohexylbutyl) amino] carbonyl]-2-oxazolyl]-7-oxabicyclo[2.2.1 ]hept-2-yl]methyl]benzenepropanoic acid, ethyl ester;

[1S-(1α,2α,3α,4α)]-2-[[3-[4-[[(cyclohexylbutyl) amino] carbonyl]-2-oxazolyl]-7-oxabicyclo[2.2.1 ]hept-2-yl]methyl-N-ethylbenzenepropanamide;

[1S-(1α,2α,3α,4α)]-2-[[3-[[(4-cyclohexylbutyl) amino] carbonyl]-2-oxazolyl]-7-oxabicyclo[2.2.1 ]hept-2-yl]methyl]benzenepropanamide;

[1S-(1α,2α,3α,4α)]-2-[[3-[4-[(phenylamino) carbonyl]-2-oxazolyl]-7-oxabicyclo[2.2.1 ]hept-2-yl]methyl]benzenepropanoic acid, or esters or salts thereof;

[1S-(1α,2α,3α,4α)]-2-[[3-[4-[(pentylmethylamino) carbonyl]-2-oxazolyl]-7-oxabicyclo[2.2.1 ]hept-2-yl]methyl] benzenepropanoic acid, or esters or salts thereof;

[1S-(1α,2α,3α,4α)]-2-[[3-[4-[(phenylamino) carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[amino (1,1'-biphenyl]-4-yl]carbonyl]-2-oxazolyl]-7-oxabicyclo 2.2.1]hept-2-yl]methyl]benzenepropanoic acid, or esters or salts thereof;

[1S-(1α,2α,3α,4α)]-2-[[3-[4-[[(4-cyclohexylbutyl) methylamino]carbonyl]-2-oxazolyl]-7-oxabicyclo[2.2.1] hept-2-yl]methyl]benzenepropanoic acid, or esters or salts thereof;

[1S-(1α,2α,3α,4α)]-2-[3-[4-[[(4-phenylbutyl) amino] carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[[4-(phenylmethoxy) phenyl]amino]carbonyl]-2-oxazolyl]-7-oxabicyclo [2.2.1 ]hept-2-yl]methyl]benzenepropanoic acid, or esters or salts thereof;

[1S-(1α,2α,3α,4α)]-2-[[3-[4-[[(hydroxyphenyl) amino] carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[[4-(4-methoxyphenyl) butyl]amino]carbonyl]-2-oxazolyl]-7-oxabicyclo [2.2.1] hept-2-yl]methyl]benzenepropanoic acid, or esters or salts thereof;

[1S-(1α,2α,3α,4α)]-2-[[3-[4-[[[4-(4-chlorophenyl) butyl] amino]carbonyl]-2-oxazolyl]-7-oxabicyclo [2.2.1]hept-2-yl]methyl]benzenepropanoic acid, or esters or salts thereof;

[1S-(1α,2α,3α,4α)]-2-[3-[4-[[(4-cyclohexylbutyl) amino]carbonyl]-2-oxazolyl]-7-oxabicyclo [2.2.1]-hept-2-yl]methyl]benzenepropanoic acid, or its potassium or sodium salts thereof;

[1S-(1α,2α,3α,4α)]-2-[[3-[4-[[(4-cyclohexylbutyl) amino]carbonyl]-2-oxazolyl]-7-oxabicyclo [2.2.1]hept-2-yl]methyl]-N-methylsulfonylbenzenepropanamide;

[1S-(1α,2α,3α,4α)]-2-[[3-[4-[[(2-propynyl)amino]carbonyl]-2-oxazolyl]-7-oxabicyclo[2.2.1]hept-2-yl]methyl]benzenepropanoic acid, or esters or salts thereof;

[1S-(1α,2α,3α(E),4α)]-2-[3-[4-[[(3-iodo-2-propenyl) amino]carbonyl]-2-oxazolyl]-7-oxabicyclo [2.2.1]hept-2-yl]methyl]benzenepropanoic acid, or esters or salts thereof;

[1S-(1α,2α,3α,4α)]-2-[[3-[4-[[4-(hydroxy-3-iodophenyl) butyl]amino]carbonyl]-2-oxazolyl]-7-oxabicyclo [2.2.1] hept-2-yl]methyl]benzenepropanoic acid, or esters or salts thereof;

[1S-(1α,2α,3α,4α)]-2-[[3-[4-[(4-cyclohexylbutyl) amino]carbonyl]-2-oxazolyl]-7-oxabicyclo [2.2.1]hept-2-yl]methyl]benzenepropanoic acid, or its monopotassium salt;

[1S-(1α,2α,3α,4α)]-2-[[3-[4-[(4-cyclohexylbutyl) amino]carbonyl]-2-oxazolyl]-7-oxabicyclo [2.2.1]hept-2-yl]methyl]benzenepropanoic acid, or its monosodium salt;

[1S-(1α,2α,3α,4α)]-2-[[3-[4-[(4-cyclohexylbutyl) amino]carbonyl]-1-H-imidazol-2-yl]-7-oxabicyclo [2.2.1] hept-2-yl]methyl]benzenepropanoic acid, or esters or salts thereof;

[1S-(1α,2α,3α,4α)]-2-[[3-[4-[[(1H-imidazol -1-yl)butylamino]carbonyl]-2-oxazolyl-7-oxabicyclo[2.2.1]hept-2-yl] methyl]benzenepropanoic acid, or esters or salts thereof;

[1S-(1α,2α,3α,4α)]-2-[[3-[4-[[[2-(4-chlorophenyl) ethyl] amino]carbonyl]-2-oxazolyl]-7-oxabicyclo [2.2.1]hept-2-yl]methyl]benzenepropanoic acid, or esters or salts thereof;

[1S-(1α,2α,3α,4α)]-2-[[3-[4-[[(1,1-dimethylethyl) amino]carbonyl]-2-oxazolyl]-7-oxabicyclo 2.2.1]hept-2-yl] methyl]benzenepropanoic acid, or esters or salts thereof;

[1S-(1α,2α,3α,4α)]-2-[[3-[4-[[(1,1-dimethylpropyl) amino]carbonyl]-2-oxazolyl]-7-oxabicyclo [2.2.1]hept-2-yl]methyl]benzenepropanoic acid, or esters or salts thereof;

[1S-(1α,2α,3α,4α)]-2-[[3-[4-[(octadecylamino) carbonyl]-2-oxazolyl]-7-oxabicyclo[2.2.1]hept-2-yl]methyl]benzenepropanoic acid, or esters or salts thereof;

[1S-(1α,2α,3α,4α)]-2-[[3-[4-[[[5-(cyclohexylamino) -5-oxopentyl]amino]carbonyl]-2-oxazolyl]-7-oxabicyclo [2.2.1]hept-2-yl]-methyl]benzenepropanoic acid, or esters or salts thereof;

[1S-(1α,2α,3α,4α)]-2-[[3-[4-[[(5-hydroxy-5-methylhexyl) amino]carbonyl]-2-oxazolyl]-7-oxabicyclo [2.2.1] hept-2-yl]methyl]benzenepropanoic acid, or esters or salts thereof;

[1S-(1α,2α,3α,4α)]-2-[3-[4-[[(5-carboxy-5-methylhexyl) amino]carbonyl]-2-oxazolyl]-7-oxabicyclo[2.2.1]hept-2-yl]methyl]benzenepropanoic acid, or esters or salts thereof;

[1S-1α,2α,3α,4α)]-2-[[3-[4-(aminocarbonyl) -2-oxazolyl]-7-oxabicyclo[2.2.1]hept-2-yl]methyl]benzenepropanoic acid, or esters or salts thereof;

[1S-(1α,2α(E),3α,4α)]-3-[2-[[3-[4-[[(4-cyclohexylbutyl) amino]carbonyl]-2-oxazolyl]-7-oxabicyclo [2.2.1]hept-2-yl]methyl]phenyl]-2-propenoic acid, or esters or salts thereof;

[1S-(1α,2α,3α,4α)]-2-[[3-[4-[[[2-[4-fluorophenyl) -1,1-dimethylethylamino]carbonyl]-2-oxazolyl]-7-oxabicyclo [2.2.1]hept-2-yl]methyl]benzenepropanoic acid, or esters or salts thereof;

[1S-(1α,2α,3α,4α]-2-[[3-[4-[[-(4-fluorophenyl) butyl] amino]carbonyl]-2-oxazolyl]-7-oxabicyclo [2.2.1]hept-2-yl]methyl]benzenepropanoic acid, or esters or salts thereof;

[1S-(1α,2α,3α,4α)]-2-[[3-[4-[[(2,2-dimethylbutyl) amino]carbonyl]-2-oxazolyl]-7-oxabicyclo [2.2.1]-hept-2-yl]methyl]benzenepropanoic acid, or esters or salts thereof;

[1S-(1α,2α,3α,4α)]-2-[[3-[4-[(2,2-dimethylpropyl) amino]carbonyl]-2-oxazolyl]-7-oxabicyclo [2.2.1]hept-2-yl]methyl]benzenepropanoic acid, or esters or salts thereof;

[1S-(1α,2α,3α,4α)]-2-[[3-[4-[[(3,3-dimethylbutyl) amino]carbonyl]-2-oxazolyl]-7-oxabicyclo [2.2.1]hept-2-yl]methyl]benzenepropanoic acid, or esters or salts thereof;

[1S-(1α,2α,3α,4α)]-2-[3-[4-[[[2-[4-fluorophenyl) ethyl] amino]carbonyl]-2-oxazolyl]-7-oxabicyclo [2.2.1]hept-2-yl]methyl]benzenepropanoic acid, or esters or salts thereof;

[1S-(1α,2α,3α,4α)]-2-[[3-[4-[[(2-phenylethyl) amino] carbonyl]-2-oxazolyl]-7-oxabicyclo-[2.2.1]hept-2-yl]methyl]benzenepropanoic acid, or esters or salts thereof;

[1S-(1α,2α,3α,4α)]-2-[[3-[4-[(6-heptynylamino]carbonyl]-2-oxazolyl]-7-oxabicyclo[2.2.1]hept-2-yl]methyl]benzenepropanoic acid, or esters or salts thereof.

Ifetroban which has the formula

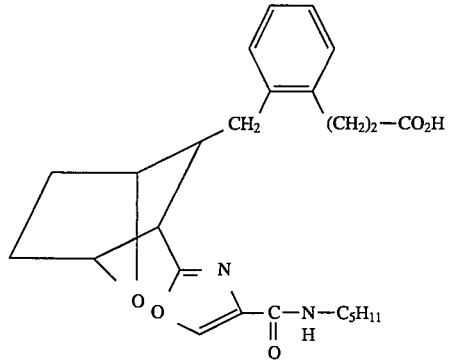

and the name [1S-(1α,2α,3α,4α)]-2-[[3-[4-[(pentylamino)carbonyl]-2-oxazolyl]-7-oxabicyclo[2.2.1]hept-2-yl]methyl]benzenepropanoic acid or a pharmaceutically acceptable salt thereof such as its sodium salt, potassium salt, calcium salt or magnesium salt, is preferred, especially the sodium salt.

In carrying out the method of the present invention, the thromboxane $A_2$ antagonist alone or in combination with the nonsteroidal anti-inflammatory compound (hereinafter referred to as the anti-inflammatory agent or compound) may be administered to mammalian species, such as dogs, cats, humans, etc., systemically, such as orally or parenterally, as well as intraperitoneally, topically, or by inhalation.

The thromboxane $A_2$ antagonist alone or in combination with the anti-inflammatory agent may be incorporated in a conventional dosage form, such as a tablet, capsule, elixir, cream, suppository, aerosol spray or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The thromboxane $A_2$ antagonist may be employed in a separate dosage form from the anti-inflammatory agent such as two separate injections and/or tablets or the two may be employed in a single dosage form, such as a single injection and/or tablet.

With regard to such systemic formulations, wherein the thromboxane $A_2$ antagonist is to be employed alone, single or divided doses of from about 0.1 to about 2500 mg, preferably from about 2 to about 2000 mg, one to six times daily, may be administered in systemic dosage forms as described above.

With regard to combinations of the thromboxane $A_2$ antagonist with anti-inflammatory agent, single or divided doses of from 0.1 to about 2500 mg of thromboxane $A_2$ antagonist, preferably 2 to 2000 mg thromboxane $A_2$ antagonist, and from about 2 to about 2000 mg anti-inflammatory agent and preferably from about 5 to about 1500 mg anti-inflammatory agent, depending upon the type of anti-inflammatory agent employed, may be administered one to six times daily.

It will be appreciated that all of the anti-inflammatory drugs disclosed herein are known for treating inflammation and/or pain and may be employed in dosage forms and amounts as disclosed in the Physicians' Desk Reference.

The following Examples represent preferred embodiments of the present invention.

EXAMPLE 1

A formulation containing the sodium salt of ifetroban, in the form of tablets for treating dysmenorrhea, having the following composition, was prepared by direct compression as described below.

| Ingredient | Percent by Weight |
| --- | --- |
| Na Salt of Ifetroban | 5.25 |
| Mannitol | 78.5 |
| Microcrystalline Cellulose | 10.0 |
| Crospovidone | 3.0 |
| Magnesium Oxide | 2.0 |
| Magnesium Stearate | 1.25 |

Na salt of ifetroban, magnesium oxide, mannitol, microcrystalline cellulose, and crospovidone were mixed together for 2 to 10 minutes employing a suitable mixer. The resulting mixture was passed through a #12 to #40 mesh size screen. Thereafter, magnesium stearate was added and mixing was continued for 1 to 3 minutes.

The resulting homogeneous mixture was then compressed into tablets each containing 5.25 mg, infetroban sodium salt.

EXAMPLE 2

A formulation containing the Na salt of ifetroban, in the form of tablets for treating dysmenorrhea, having the following composition was prepared by direct compression as described in Example 1.

| Ingredient | Percent by Weight |
| --- | --- |
| Na Salt of Ifetroban | 5.25 |
| Mannitol | 60.75 |
| Microcrystalline Cellulose | 20.0 |
| Pregelatinized Starch | 10.0 |
| Magnesium Oxide | 2.0 |
| Sodium Stearyl Fumarate | 2.0 | except that pregelatinized starch and Na stearyl fumarate were employed in place of crospovidone and Mg stearate.

EXAMPLE 3

An ifetroban sodium salt formulation in the form of tablets for treating dysmenorrhea, each containing about 1 mg ifetroban sodium salt, having the following composition was prepared by a wet granulation procedure.

| Ingredient | Percent by Weight |
| --- | --- |
| Na Salt of Ifetroban | 1.05 |
| Dicalcium Phosphate Dihydrate | 85.95 |
| Pregelatinized Starch | 10.0 |
| Magnesium Oxide | 2.0 |
| Magnesium Stearate | 1.0 |

EXAMPLE 4

A ifetroban sodium salt formulation in the form of tablets for treating dysmenorrhea, each containing 1.05 mg ifetroban sodium salt, having the following composition, was prepared by a wet granulation procedure.

| Ingredient | Percent by Weight |
| --- | --- |
| Na Salt of Ifetroban | 1.05 |
| Mannitol | 51.95 |
| Microcrystalline Cellulose | 31.0 |
| Pregelatinized Starch | 10.0 |
| Calcium Carbonate | 1.0 |
| Crospovidone | 4.0 |
| Magnesium Stearate | 1.0 |

EXAMPLE 5

An ifetroban sodium salt formulation in the form of tablets for treating dysmenorrhea, each containing 20 mg ifetroban sodium salt, having the following composition was prepared by the first wet granulation technique.

| Ingredient | Percent by Weight |
| --- | --- |
| Na Salt of Ifetroban | 20.0 |
| Lactose | 45.0 |
| Starch | 20.0 |
| Aluminum Hydroxide | 10.0 |
| Povidone | 2.5 |
| Ferric Oxide | 0.5 |
| Magnesium Stearate | 1.5 |
| Colloidal Silicon Dioxide | 0.5 |

EXAMPLE 6

An ifetroban sodium salt formulation in the form of tablets for treating dysmenorrhea, each containing about 10.5 mg ifetroban sodium salt, having the following composition, was prepared by a dry granulation technique.

| Ingredient | Percent by Weight |
| --- | --- |
| Na Salt of Ifetroban | 10.5 |
| Mannitol | 74.75 |
| Microcrystalline Cellulose | 10.0 |
| Crospovidone | 4.0 |
| Sodium Bicarbonate | 0.5 |
| Magnesium Stearate | 0.25 |

EXAMPLE 7

An ifetroban sodium salt formulation in the form of tablets for treating dysmenorrhea, each containing 35 mg ifetroban sodium salt, having the following composition was prepared by a dry granulation technique.

| Ingredient | Percent by Weight |
| --- | --- |
| Na Salt of Ifetroban | 35.0 |
| Mannitol | 50.2 |
| Microcrystalline Cellulose | 8.0 |
| Crospovidone | 3.0 |
| Magnesium Oxide | 2.0 |
| Colloidal Silicon Dioxide | 0.3 |
| Magnesium Stearate | 1.5 |

EXAMPLE 8

A film coated tablet, for treating dysmenorrhea, containing 5.1 mg ifetroban sodium salt having the following composition was prepared as follows.

| Ingredient | Percent by Weight of Coated Tablet |
| --- | --- |
| Na Salt of Ifetroban | 5.1 |
| Mannitol | 76.2 |
| Microcrystalline Cellulose | 9.7 |
| Crospovidone | 2.9 |
| Magnesium Oxide | 1.9 |
| Magnesium Stearate | 1.2 |
| Film Coating | |
| Hydroxypropylmethyl Cellulose | 1.7 |
| 1,2,3-Propanetriol Triacetate | 0.7 |
| Ferric Oxide | 0.3 |
| Titanium Dioxide | 0.3 |

The tablet core was prepared as described in Example 1.

The film coated tablets were prepared by dissolving or suspending the film coating ingredients in water and then spraying the coating solution on the core tablets.

EXAMPLE 9

A film coated tablet, for treating dysmenorrhea, containing 34 mg ifetroban sodium salt having the following composition was prepared as follows.

| Ingredient | Percent by Weight of Coated Tablet |
|---|---|
| Na Salt of Ifetroban | 34.0 |
| Mannitol | 48.7 |
| Microcrystalline Cellulose | 7.8 |
| Crospovidone | 2.9 |
| Magnesium Oxide | 1.9 |
| Colloidal Silicon Dioxide | 0.3 |
| Magnesium Stearate | 1.2 |
| Film Coating | |
| OPADRY ™ | 3.2 |

The tablet core was prepared as described in Example 1.

The film coated tablets were prepared by dissolving or suspending the film coating ingredients in water and then spraying the coating solution on the core tablets.

EXAMPLE 10

An ifetroban sodium salt formulation for treating dysmenorrhea was prepared in the form of capsules, each containing 5.25 mg ifetroban sodium salt and magnesium oxide alkalizing agent, having the following composition.

| Example 10 Formulation (With MgO Alkalizing Agent) | |
|---|---|
| Ingredient | Percent by Weight |
| Na Salt of Ifetroban | 5.25 |
| Dicalcium Phosphate Dihydrate | 82.25 |
| Pregelatinized Starch | 10.0 |
| Magnesium Oxide | 2.0 |
| Magnesium Stearate | 0.5 |

EXAMPLE 11

A thromboxane $A_2$ antagonist formulation suitable for oral administration for use in treating dysmenorrhea is set out below.

1000 tablets each containing 400 mg of thromboxane $A_2$ receptor antagonist (ifetroban) were produced from the following ingredients.

| | |
|---|---|
| Na Salt of Ifetroban | 400 g |
| Corn starch | 50 g |
| Gelatin | 7.5 g |
| Avicel (microcrystalline cellulose) | 25 g |
| Magnesium stearate | 2.5 g |

The ifetroban and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

EXAMPLE 12

An injectable solution of thromboxane $A_2$ receptor antagonist for intravenous use in treating dysmenorrhea is produced as follows.

| | |
|---|---|
| Na Salt of Ifetroban | 2500 mg |
| Methyl paraben | 5 mg |
| Propyl paraben | 1 mg |
| Sodium Chloride | 25 g |
| Water for injection qs. | 5 l |

The thromboxane $A_2$ receptor antagonist, preservatives and sodium chloride are dissolved in 3 liters of water for injection and then the volume is brought up to 5 liters. The solution is filtered through a sterile filter and asceptically filled into presterilized vials which are then closed with presterilized rubber closures. Each vial contains a concentration of 75 mg of active ingredient per 150 ml of solution.

EXAMPLE 13

Tablets for use in treating dysmenorrhea are prepared as described in Example 1 except that the thromboxane $A_2$ receptor antagonist employed is [1S($\alpha$,2$\alpha$,3$\alpha$,4$\alpha$)]-2-[[3-[4-[(4-cyclcohexylbutylamino) carbonyl]-2-oxazolyl]-7-oxabicyclo[2.2.1]hept-2-yl]-methyl]benzenepropanoic acid.

EXAMPLE 14

A thromboxane $A_2$ antagonist tablet formulation suitable for oral administration is set out below.

1000 tablets each containing 40 mg of thromboxane $A_2$ receptor antagonist are produced from the following ingredients.

| | |
|---|---|
| [1S-(1$\alpha$,2$\alpha$,3$\alpha$,4$\alpha$)]-2-[[3-[4-[[(4-chlorophenyl)butyl]amino]carbonyl]-2-oxazolyl]-7-oxabicyclo[2.2.1]-hept-2-yl]methyl]benzenepropanoic acid | 40 g |
| Corn starch | 50 g |
| Gelatin | 7.5 g |
| Avicel (microcrystalline cellulose) | 25 g |
| Magnesium stearate | 2.5 g |

The thromboxane $A_2$ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 40 mg of active ingredient.

EXAMPLE 15

The following ifetroban sodium salt tablet formulation for treating dysmenorrhea is prepared as described below.

| Ifetroban Tablets (50 mg free acid) | | |
|---|---|---|
| Composition | | Amount (mg/tablet) |
| Na Salt of Ifetroban | ca. | 52.5 |
| Microcrystalline cellulose, NF | ca. | 39.4 |
| Mannitol, USP | ca. | 15.0 |
| Pregelatinized starch NF | ca. | 11.3 |
| Crospovidone, NF | ca. | 3.8 |
| Magnesium oxide, USP | ca. | 0.6 |
| Colloidal silicon dioxide, NF | ca. | 0.6 |
| Magnesium stearte, NF | ca. | 1.9 |

The above tablet formulation was prepared by a modified wet granulation procedure as described below.

The microcrystalline cellulose is mixed with magnesium oxide, a portion of pregelatinized starch, and a portion of crospovidone and the mixture is wet granulated with water to form a wet powder mass.

The ifetroban sodium salt is mixed with the wet powder mass and the resulting granules are dried.

The dried granulation is reduced to desired particle size, and the resulting granules are mixed with mannitol, colloidal silicon dioxide, the remaining pregelatinized starch and the remaining crospovidone. The above blend is mixed with magnesium stearate and the resulting mix is compressed into tablets.

EXAMPLE 16 TO 29

The formulations as described in Examples 1 to 15 are prepared except that 650 mg of aspirin was included in each tablet or dose equivalent.

EXAMPLE 30 TO 43

The formulations as described in Examples 1 to 15 are prepared except that 50 mg of indomethacin was included in each tablet or dose equivalent.

EXAMPLE 44 TO 57

The formulations as described in Examples 1 to 15 are prepared except that 50 mg of meclofenamate was included in each tablet or dose equivalent.

EXAMPLE 58 TO 71

The formulations as described in Examples 1 to 15 are prepared except that 50 mg of ibuprofen was included in each tablet or dose equivalent.

EXAMPLE 72 TO 85

The formulations as described in Examples 1 to 15 are prepared except that 250 mg of naproxen was included in each tablet or dose equivalent.

What is claimed is:

1. A method for treating dysmenorrhea in a mammalian species, which comprises administering to a mammalian species in need of such treatment a therapeutically effective amount of a thromboxane $A_2$ receptor antagonist, which is an interphenylene 7-oxabicycloheptyl substituted heterocyclic amide prostaglandin analog and has the formula

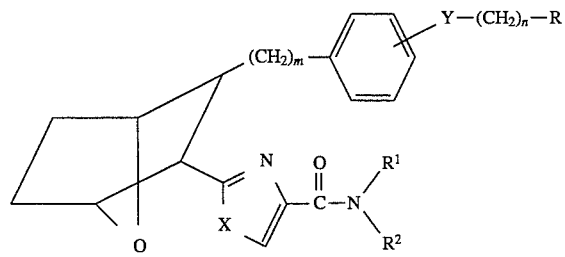

and including all stereoisomers thereof, wherein
  m is 1, 2 or 3; n is 0, 1, 2, 3 or 4;
  Y is O or a single bond, with the proviso that when n is 0, Y is a single bond;
  R is $CO_2H$, $CO_2$lower alkyl, $CO_2$alkali metal, $CH_2OH$, $CONHR^{3a}$, $CONHSO_2R^3$ or 5-tetrazolyl, with the proviso that when R is 5-tetrazolyl, n cannot be 0;
  X is O, S or NH;

$R^1$ is H, lower alkyl, aryl, cycloalkyl, lower alkenyl, lower alkynyl, aralkyl, cycloalkylalkyl, cycloheteroalkyl, cycloheteroalkylalkyl, heteroaryl, heteroarylalkyl or an amide;

$R^2$ is hydrogen, lower alkyl, aryl, or aralkyl; or $R^1$ and $R^2$ together with the nitrogen to which they are linked may form a 5- to 8-membered ring;

$R^3$ is lower alkyl, aryl or aralkyl; and $R^{3a}$ is H, lower alkyl, aryl or aralkyl.

2. The method as defined in claim 1 wherein the interphenylene 7-oxabicycloheptyl substituted heterocyclic amide prostaglandin has the formula

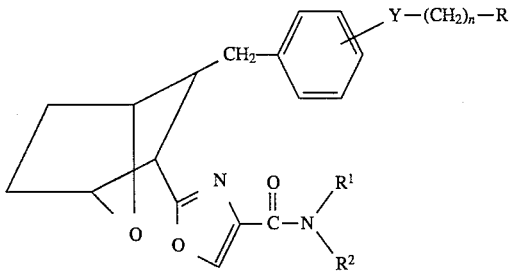

3. The method as defined in claim 1 wherein the thromboxane $A_2$ receptor antagonist is [1S-(1α,2α,3α,4α)]-2-[[3-[4-[[(4-cyclohexylbutyl) amino]carbonyl]-2-oxazolyl]-7-oxabicyclo[2.2.1]hept-2-yl]methyl]benzenepropanoic acid or an ester or salt thereof; [1S-(1α,2α,3α,4α)]-2-[[3-[4-[[(4-chlorophenyl) butyl]amino]carbonyl]-2-oxazolyl]-7-oxabicyclo[2.2.1]hept -2-yl]methyl]benzenepropanoic acid or an ester or salt thereof; [1S-(1α,2α,3α,4α)]-3-[[3-[4-[[(4-cyclohexylbutyl) amino]carbonyl]-2-oxazolyl]-7-oxabicyclo[2.2.1]hept-2-yl]methyl]benzeneacetic acid, or an ester or salt thereof; [1S-(1α,2α,3α,4α)]-2-[[[3-[4-[[(4-cyclohexylbutyl) amino]carbonyl]-2-oxazolyl]-7-oxabicyclo [2.2.1]hept-2-yl]methyl]phenoxy]acetic acid, or an ester or salt thereof; or [1S-(1α,2α,3α,4α)]-2-[[3-[4-[[(4-dimethyloctyl) amino]carbonyl]-2-oxazolyl]-7-oxabicyclo[2.2.1] hept-2-yl]methyl]benzenepropanoic acid, or an ester or salt thereof.

4. The method as defined in claim 1 wherein the thromboxane $A_2$ receptor antagonist is ifetroban or its sodium, potassium, calcium or magnesium salt.

5. The method as defined in claim 1 wherein the thromboxane $A_2$ receptor antagonist is ifetroban, sodium salt.

6. The method as defined in claim 5 wherein the thromboxane $A_2$ receptor antagonist is employed in a weight ratio to the non-steroidal anti-inflammatory drug of within the range of from about 0.01:1 to about 100:1.

7. The method as defined in claim 1 wherein the thromboxane $A_2$ receptor antagonist is administered in combination with a non-steroidal anti-inflammatory drug.

8. The method as defined in claim 7 wherein the thromboxane $A_2$ antagonist is ifetroban or its sodium, potassium, calcium or magnesium salt.

9. The method as defined in claim 7 wherein the thromboxane $A_2$ antagonist is ifetroban, sodium salt.

10. The method as defined in claim 7 wherein the anti-inflammatory agent is aspirin, indomethacin, naproxen, ibuprofen, meclofenamate, phenylbutazone, diclofenac sodium or piroxicam.

11. The method as defined in claim 7 wherein the thromboxane receptor antagonist is ifetroban, sodium salt and the anti-inflammatory compound is aspirin or indomethacin.

12. A method for treating dysmenorrhea in a mammalian species, which comprises administering to a mammalian species in need of such treatment a therapeutically effective amount of a thromboxane $A_2$ receptor antagonist which is an interphenylene 7-oxabicycloheptyl substituted heterocyclic amide prostaglandin analog and has the formula

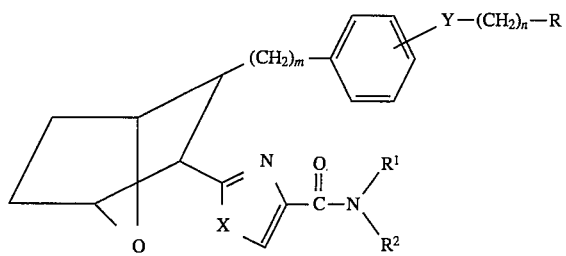

and including all stereoisomers thereof, wherein m is 1, 2 or 3; n is 0, 1, 2, 3 or 4;

Y is O or a single bond, with the proviso that when n is 0, Y is a single bond;

R is $CO_2H$, $CO_2$lower alkyl, $CO_2$alkali metal, $CH_2OH$, $CONHR^{3a}$, $CONHSO_2R^3$ or 5-tetrazolyl, with the proviso that when R is 5-tetrazolyl, n cannot be 0;

X is O, S or NH;

$R^1$ is H, lower alkyl, aryl, cycloalkyl, lower alkenyl, lower alkynyl, aralkyl, cycloalkylalkyl, cycloheteroalkyl, cycloheteroalkylalkyl, heteroaryl, heteroarylalkyl or an amide;

$R^2$ is hydrogen, lower alkyl, aryl, or aralkyl; or $R^1$ and $R^2$ together with the nitrogen to which they are linked may form a 5- to 8-membered ring;

$R^3$ is lower alkyl, aryl or aralkyl; and $R^{3a}$ is H, lower alkyl, aryl or aralkyl, and a non-steroidal anti-inflammatory drug.

13. The method as defined in claim 12 wherein the interphenylene 7-oxabicycloheptyl substituted heterocyclic amide prostaglandin analog has the formula

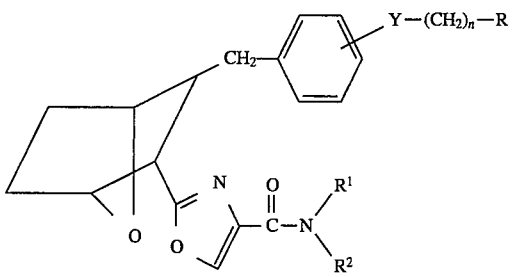

and including all stereoisomers thereof, wherein m is 1, 2 or 3; n is 0, 1, 2, 3 or 4;

R is $CO_2H$, $CO_2$lower alkyl, $CO_2$alkali metal, $CH_2OH$, $CONHR^{3a}$, $CONHSO_2R^3$ or 5-tetrazolyl, with the proviso that when R is 5-tetrazolyl, n cannot be 0;

$R^1$ is H, lower alkyl, aryl, cycloalkyl, lower alkenyl, lower alkynyl, aralkyl, cycloalkylalkyl, cycloheteroalkyl, cycloheteroalkylalkyl, heteroaryl, heteroarylalkyl or an amide;

$R^2$ is hydrogen, lower alkyl, aryl, or aralkyl; or $R^1$ and $R^2$ together with the nitrogen to which they are linked may form a 5- to 8-membered ring;

$R^3$ is lower alkyl, aryl or aralkyl; and $R^{3a}$ is H, lower alkyl, aryl or aralkyl.

14. The method as defined in claim 12 wherein the non-steroidal anti-inflammatory drug is aspirin, indomethacin, naproxen, ibuprofen, meclofenamate, phenylbutazone, diclofenac sodium, piroxicam or a corticosteroid.

15. The method as defined in claim 12 wherein the thromboxane $A_2$ antagonist is ifetroban, sodium salt, potassium salt, calcium salt or magnesium salt.

* * * * *

UNITED STATES PATENT AND TRADEMARK OFFICE
CERTIFICATE OF CORRECTION

PATENT NO.  : 5,605,917
DATED       : February 25, 1997
INVENTOR(S) : Martin L. Ogletree It is certified that error appears in the above-identified patent and that said Letters Patent is hereby corrected as shown below:

Col. 14, line 15, "$CH_2$" linking the oxabicycloheptyl ring and the benzene ring should be $--(CH_2)_m--$.

Col. 16, line 3, "$CH_2$" linking the oxabicycloheptyl ring and the benzene ring should be $--(CH_2)_m--$.

Signed and Sealed this

Twelfth Day of August, 1997

Attest:

BRUCE LEHMAN

Attesting Officer        Commissioner of Patents and Trademarks